United States Patent
Weissman et al.

(10) Patent No.: US 6,576,448 B2
(45) Date of Patent: Jun. 10, 2003

(54) METHODS FOR SELECTIVELY ISOLATING DNA USING ROLLING CIRCLE AMPLIFICATION

(75) Inventors: Sherman Weissman, New Haven, CT (US); Roger Lasken, Guilford, CT (US)

(73) Assignees: Molecular Staging, Inc., New Haven, CT (US); Yale University, New Haven, CT (US)

(*) Notice: Subject to any disclaimer, the term of this patent is extended or adjusted under 35 U.S.C. 154(b) by 8 days.

(21) Appl. No.: 09/818,927

(22) Filed: Mar. 28, 2001

(65) Prior Publication Data

US 2002/0076704 A1 Jun. 20, 2002

Related U.S. Application Data

(62) Division of application No. 09/398,216, filed on Sep. 17, 1999, now Pat. No. 6,235,502.
(60) Provisional application No. 60/100,996, filed on Sep. 18, 1998.

(51) Int. Cl.[7] ............................ C12P 19/34; C12Q 1/68; G01N 33/00; C07H 21/02; C07H 21/04
(52) U.S. Cl. .................... 435/91.2; 435/6; 435/91.1; 436/94; 536/23.1; 536/24.3; 536/24.33
(58) Field of Search .......................... 435/6, 91.1, 91.2, 435/183; 436/94; 536/23.1, 24.3, 24.33, 25.3, 25.32

(56) References Cited

U.S. PATENT DOCUMENTS

| | | |
|---|---|---|
| 5,556,750 A | 9/1996 | Modrich et al. |
| 6,010,850 A | 1/2000 | Weissman et al. ............ 435/6 |
| 6,287,824 B1 * | 9/2001 | Lizardi ..................... 435/91.2 |

OTHER PUBLICATIONS

Nelson, Nature Genetics (1993), vol. 4:11–18.
Straus et al. "Genomic subtraction for cloning DNA corresponding to delection mutations" Proc. Natl. acad. Sci. vol. 87, pp. 1889–1893, Mar. 1990.
McAllister et al. "Ernrichment for Loci Identical–by Descent between pairs of Mouse or Human genomes by Genomic Mismatch Scanning" Genomics, vol. 47, pp. 7–11, Jan. 1998.
Riley et al. "A novel, rapid method for the isolation of terminal sequneces from YAC clones" Nucleic Acid Research, vol. 18, No. 10, pp. 2887–2890, 1990.
Cheung et al. "Genomic Mismatch Scanning: Applications to linkage and linkage disequilibrium analysis" Am. J. of Human Genetics, vol. 61, No. 4, Suppl. p. A271, Oct. 1997.
Prasher & Weissman Proc. Nat. Acad. USA (1996) 93:659–663.
Geung et al. Nature Genetics (1998), 18: 225–230.

* cited by examiner

*Primary Examiner*—Ethan Whisenant
*Assistant Examiner*—Frank Lu
(74) *Attorney, Agent, or Firm*—Banner & Witcoff, Ltd.

(57) ABSTRACT

DNA containing nucleotide base mispairs can be isolated using a modified rolling circle amplification procedure. Specific Y-shaped adapters permit the selective circularization of these fragments with a complementary splint oligonucleotide. Rolling circle amplification is then carried out with a DNA polymerase. Rolling circle amplification can also be carried out using a mixture of DNA circles having different lengths. Genetic phase of linked DNA markers can be determined by selective amplification of one parental haplotype. DNA fragments can also be converted into a form that can be utilized as rolling circle amplification templates by ligation of hairpin forming adapters to the ends of the fragments. Two or more DNA polymerases can be used in a rolling circle amplification reaction. DNA polymerase III has special properties that improve rolling circle amplification.

6 Claims, 9 Drawing Sheets

FIG. 1E
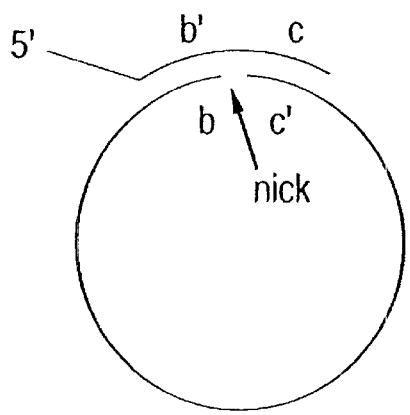
FIG. 1F
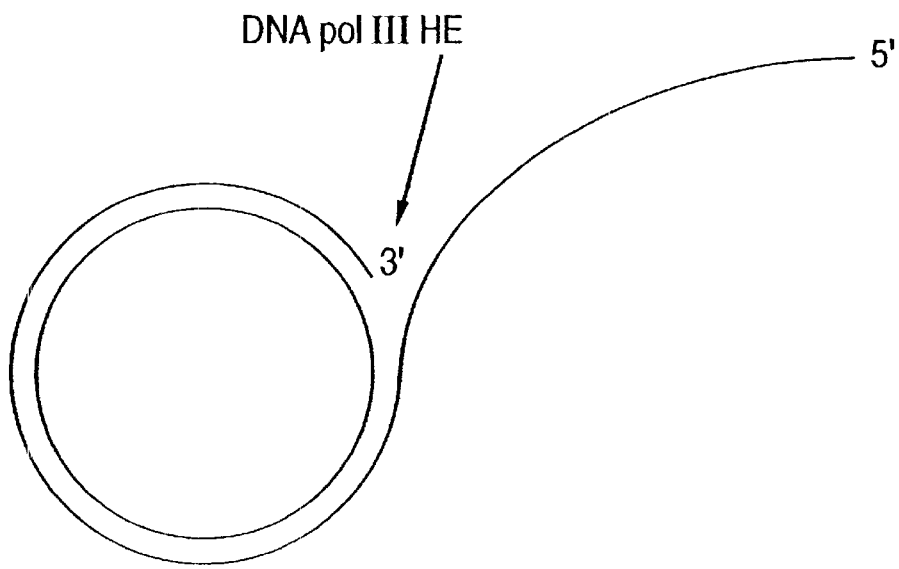

FIG. 1J
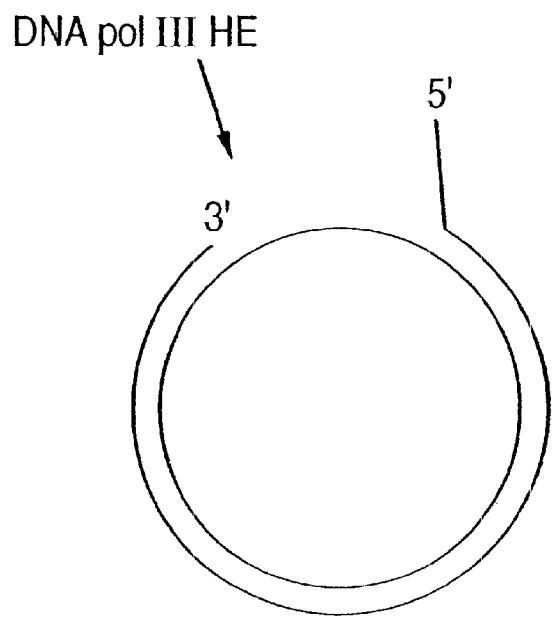
DNA pol III HE
FIG. 1K
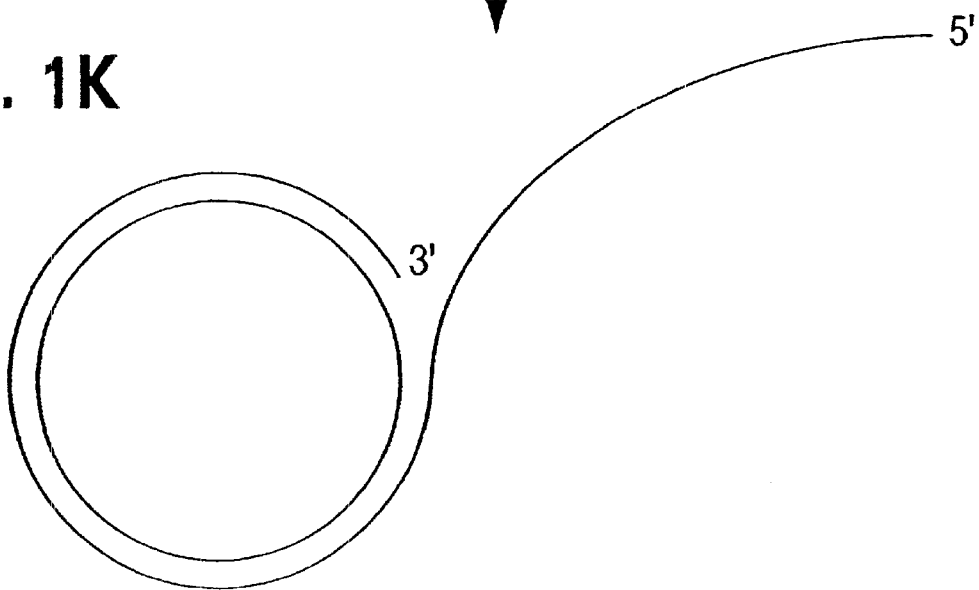

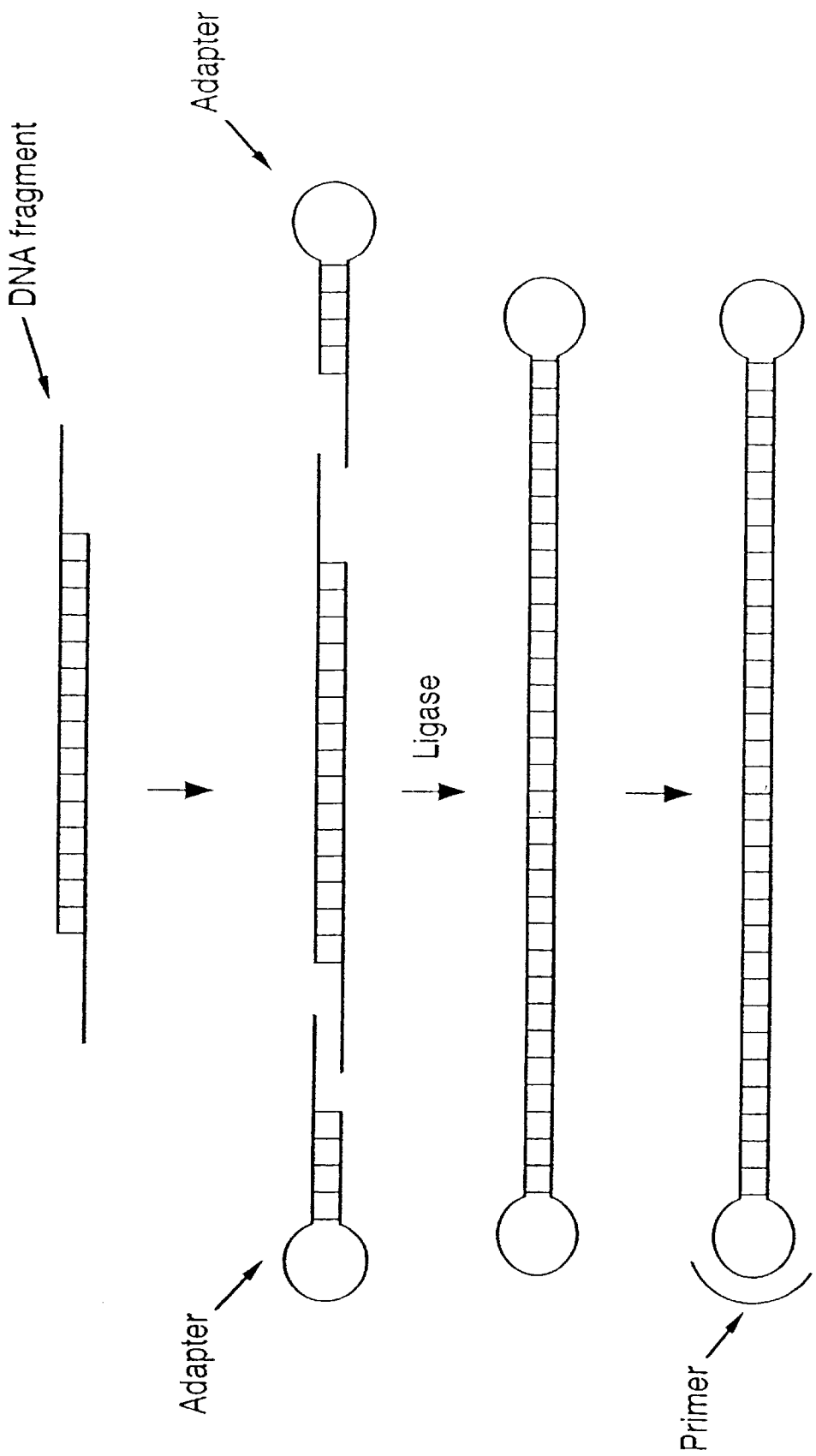

The Effect of dNTP Concentration and T7 Native DNA Polymerase on RCA by Sequenase

METHODS FOR SELECTIVELY ISOLATING DNA USING ROLLING CIRCLE AMPLIFICATION

This application is a Divisional of Ser. No. 09/398,216, filed Sep. 17, 1999, now U.S. Pat. No. 6,235,502 and the benefit of application Ser. No. 60/100,996, filed Sep. 18, 1998.

TECHNICAL FIELD OF THE INVENTION

This invention relates to methods for amplifying DNA sequences, including those selected in genome mismatch scanning procedures, through the use of rolling circle DNA amplification. Methods of the invention are useful in genotyping, phase determination, polymorphism analyses, mismatch scanning procedures, and general cloning procedures.

BACKGROUND OF THE INVENTION

Rolling circle amplification (RCA) is an isothermal process for generating multiple copies of a sequence. In rolling circle DNA replication in vivo, a DNA polymerase extends a primer on a circular template (Komberg, A. and Baker, T. A. *DNA Replication,* W. H. Freeman, New York, 1991). The product consists of tandemly linked copies of the complementary sequence of the template. RCA is a method that has been adapted for use in vitro for DNA amplification (Fire, A. and Si-Qun Xu, *Proc. Natl. Acad Sci. USA,* 1995, 92:4641–4645; Lui, D., et al., *J. Am. Chem. Soc.,* 1996, 118:1587–1594; Lizardi, P. M., et al., *Nature Genetics,* 1998, 19:225–232; U.S. Pat. No. 5,714,320 to Kool). RCA can also be used in a detection method using a probe called a "padlock probe" (WO Pat. Ap. Pub. 95/22623 to Landegren; Nilsson, M., et al. *Nature Genetics,* 1997, 16:252–255, and Nilsson, M., and Landegren, U., in Landegren, U., ed., *Laboratory Protocols for Mutation Detection,* Oxford University Press, Oxford, 1996, pp. 135–138). DNA synthesis has been limited to rates ranging between 50 and 300 nucleotides per second (Lizardi, cited above and Lee, J., et al., *Molecular Cell,* 1998, 1: 1001–1010).

In some embodiments of this invention, increased rates of DNA synthesis in RCA are achieved by the use of DNA polymerase III holoenzyme (also referred to herein as pol III) which has an intrinsic catalytic rate of about 700–800 nucleotides per second (Kornberg and Baker, cited above). The invention also applies to subassemblies of the pol III holoenzyme which lack one or more of the subunits found in the complete, native enzyme complex (Kornberg and Baker, cited above). The invention applies to DNA polymerase III holoenzyme derived from *E. coli* and also other bacteria, including gram-positive and gram-negative bacteria, or related DNA polymerases from eukaryotes that have clamp (PCNA) and clamp loader (RFC) components (Kornberg and Baker, cited above). These pol III-like DNA polymerases are evolutionarily distinguished from pol I-type enzymes (Braithwaite, D. K., and Ito, J., *Nuc. Acids Res.,* 1993, 21:787–802.) that have previously been employed in RCA (Fire and Xu, Lui, D. et al., Lizardi et al., and Lee et al., all cited above).

Therefore, this invention introduces the novel use of a distinct class of DNA polymerases that have not previously been used in RCA. The methods are applicable to polymorphism detection, diagnostics, phase determination, genotyping, genomic mapping, DNA sequencing, synthesis of DNA probes, or cloning. The high rate of synthesis, great processivity, and ability to replicate through sequence obstructions give pol III an advantage over other DNA polymerases in RCA. The *E. coli* dnab, dnaG, and dnaC proteins or other helicases and the single-stranded DNA binding protein (SSB) can also be used to facilitate the reaction (Kornberg and Baker, cited above). This invention applies to the use of pol III with any accessory proteins including helicases, primases, and DNA binding proteins that facilitate the pol III reaction.

In another embodiment of the invention two or more DNA polymerases are combined in one RCA reaction. One of the polymerases may have a 3'→5' exonuclease activity capable of removing mismatched nucleotides. Such combinations of DNA polymerases are known to increase primer extension. (Cheng, S. et al., *Proc. Natl. Acad. Sci. USA,* 1994, 91:5695–5699.)

This invention further provides for a method to produce approximately equimolar rolling circle amplification of DNA fragment mixtures. The method is applicable to RCA of any DNA including for purposes of detection, cloning, generation of probes, genetic mismatch scanning (GMS) procedures, DNA mapping, sequencing, and genotyping. In an RCA using mixed circular DNA templates of different length, a greater number of copies of shorter circles will be generated relative to longer circles. This effect is reduced by creating a "slow step" or "pause site" that occurs once each time the DNA polymerase copies around the circle. Therefore, the DNA polymerase rapidly copies around the circles and then it pauses for the slow step before copying around the circle again. The number of copies made of each circle will tend to be the same, independent of the length of the circle. In one procedure, the pause site is created by the introduction of one or more abasic sites in the template. DNA polymerases are slowed but not completely blocked by such a site. They will tend to insert a nucleotide opposite the abasic site Randell, S. K., et al., *J. Biol. Chem.,* 1987, 262:6864–6870).

In one embodiment of this invention, DNA fragments selected with genomic mismatch scanning are amplified by RCA. In 1993 Nelson and associates described and employed GMS to directly identify identical-by-descent (IBD) sequences in yeast (Nelson, S. F., et al., *Nature Genetics,* 1993, 4:11–18). The method allows DNA fragments from IBD regions between two relatives to be isolated based on their ability to form mismatch-free hybrid molecules. The method consists of digesting DNA fragments from two sources with a restriction endonuclease that produces protruding 3'-ends. The protruding 3'-ends provide some protection from exonuclease III (Exo III), which is used in later steps. The two sources are distinguished by methylating the DNA from only one source. Molecules from both sources are denatured and reannealed, resulting in the formation of four types of duplex molecules: homohybrids formed from strands derived from the same source and heterohybrids consisting of DNA strands from different sources. Heterohybrids can either be mismatch-free or contain base-pair mismatches, depending on the extent of identity of homologous regions.

Homohybrids are distinguished from heterohybrids by use of restriction endonucleases that cleave fully methylated or unmethylated GATC sites. Homohybrids are cleaved into smaller duplex molecules. Heterohybrids containing a mismatch are distinguished from mismatch-free molecules by use of the *E. coli* methyl-directed mismatch repair system. The combination of three proteins of the system MutS, MutL, and MutH (herein collectively called MutSLH) along with ATP introduce a single-strand nick on the unmethylated strand at GATC sites in duplexes that contain a mismatch (Welsh, et al., *J. Biol. Chem.*, 1987, 262:15624). Heterohybrids that do not contain a mismatch are not nicked. All molecules are then subjected to digestion by Exo III, which can initiate digestion at a nick, a blunt end, or a recessed 3'-end, to produce single-stranded gaps. Only mismatch-free heterohybrids are not subject to attack by Exo III; all other molecules have single-stranded gaps introduced by the enzyme. Molecules with single-stranded regions are removed by absorption to benzoylated napthoylated DEAE cellulose. The remaining molecules consist of mismatch-free heterohybrids which may represent regions of IBD.

SUMMARY OF THE INVENTION

Methods are given for isolating DNA containing nucleotide base mispairs using a modified rolling circle amplification procedure. DNA fragments containing the base mismatches are nicked by conventional genomic mismatch scanning methods. The 3'-OH at the nick serves as a primer for DNA synthesis. The 3'-end is elongated by a DNA polymerase possessing strand displacement or nick translation capacity, or by a combination of a DNA polymerase capable of strand displacing at a nick and DNA polymerase III holoenzyme which provides a high rate of processive DNA synthesis. Specific Y-shaped adapters attached to the ends of the fragments are designed such that DNA products generated by the extension of the 3'-OH at the nick have a unique sequence at their 3'-end. The unique sequences allow for the selective circularization of these fragments with a complementary splint oligonucleotide. Rolling circle amplification is then carried out with a DNA polymerase. DNA polymerase III holoenzyme (herein referred to as pol III or pol III holoenzyme) is used to provide a superior rate of DNA synthesis and also high processivity which allows rapid replication through regions of high GC content, hairpin structures and other regions of secondary structure, and regions that normally slow replication due to local sequence context effects. The *E. coli* dnaB, dnaG, and dnaC gene products or other DNA helicases and the single-stranded DNA binding protein (SSB) are also used to improve the reaction. The use of pol III or pol III combined with other replication proteins is generally applicable to any RCA procedure in addition to methods specifically relating to GMS procedures. In another method that improves any RCA reaction in general, two DNA polymerases are combined together. One of the polymerases has a 3'→5' exonuclease activity capable of removing misincorporated nucleotides.

In addition, methods are given for carrying out rolling circle amplification of a mixture of DNA circles having different lengths. In general, more copies will tend to be made for shorter circles because the DNA polymerase requires less time to replicate them. For some procedures, including the amplification of DNA for cloning or detection purposes, or for genomic mismatch scanning, it is desirable to produce approximately equal numbers of all circles independent of their length. This is accomplished by creating a slow step in the replication process. Therefore, replication stops for a period of time once each time the DNA polymerase copies around the circle. The result of having one slow step for each copy of the circle that is synthesized is that the rate-limiting step for the amplification tends to be the same regardless of the length of the circle. This tends to minimize the disparity between the number of copies made for circles of different length. The "slow step" is created by introducing a site on the DNA sequence where the DNA polymerase is slowed or otherwise partially obstructed. A slowing of the rate of DNA polymerization is typically created at so-called "pause sites" at naturally occurring sequences where the local DNA structure is unfavorable for replication, or by introducing abasic sites which require longer times for the insertion of nucleotides by the DNA polymerase. Several types of potential pause sites are described herein. An alternative approach is to completely block the DNA polymerase with a reversible obstruction so that replication can be repeatedly stopped and then continued. For example, a properly designed hairpin structure can block replication at a low temperature while elevation to a higher temperature can be repeatedly used to allow the next cycle of DNA synthesis.

Methods are also given for determining the genetic phase of linked DNA markers by selective amplification of one parental haplotype. Several procedures are given for cutting DNA to create the target fragment to be analyzed, and circularizing the target DNA. Alternative procedures are also used to prime the DNA synthesis used for RCA. By circularizing the target fragment with an adapter for which only one of its strands can be ligated, a nick with a 3'-OH is created in the DNA circle that can serve as a primer for initiating rolling circle amplification. By using an adapter which has an internal single-stranded region and which also has double-stranded ends with appropriate overhangs for ligation to the target DNA, a single-stranded gap is introduced into the circularized adapter-fragment construct. This gap can be employed as a site for primer annealing facilitating the initiation of rolling circle amplification. The 3'-OH of the gap itself can also serve as a primer.

The single-stranded DNA product of rolling circle amplification can itself be replicated by annealing of complementary primers which can be extended in conventional primer elongation reactions or in hyberbranching reactions in which exponential amplification occurs (Lizardi, cited above). By choosing primers with 3'-ends complementary to one of two alleles, the DNA synthesis can be used for detection purposes. DNA polymerase III or DNA pol II derived from *E. coli* or other bacteria, or analogous polymerase complexes from eukaryotic organisms that also have clamp and clamp loader components (Kelman, Z., and O'Donnell, M., *Annu. Rev. Biochem.*, 1995, 64:171–200, Bloom, L. B., et al., *J. Biol. Chem.*, 1997, 272:27919–27930, and Kelman, Z., et al., *Structure*, 1998, 6:121–125) are used to facilitate amplification of DNA targets including large fragments that are difficult to replicate with other enzymes. DNA pol III is used to provide a superior rate of DNA synthesis and also high processivity which allows rapid replication through regions of high GC content, hairpin structures and other regions of secondary structure, and regions that normally slow replication due to local sequence context effects. DNA helicases such as the dnaB gene product and SSB of *E. coli* can be used to further improve rate and strand displacement. The superior performance of DNA pol III to other DNA polymerases gives an advantage in any genotyping, DNA mapping, DNA sequencing, or cloning work in which large DNA fragments, 1 kb to greater than a megabase in length are used, and also for shorter fragments where rate or strand displacement is important.

In addition, methods are given for converting DNA fragments into a form that can be utilized as RCA templates by ligation of hairpin forming adapters to the ends of the fragments. The adapters have 3' and 5' ends that are complementary to each other such that they form stem and loop structures. Furthermore, the stem portion of the hairpin structures create blunt or overhanging ends that allow the adapter to be ligated to the end of any DNA fragments having the appropriate end. By ligating such adapters to both ends of the DNA fragments, the fragments are converted to a circular form which can be utilized as the template for an RCA reaction. Also, the loop portion of the adapters provide a single-stranded region to which the RCA primer can be annealed.

Another invention uses two or more DNA polymerases in an RCA reaction. At least one of the DNA polymerases possesses a 3'–5' exonuclease proofreading activity capable of correcting base mispairs. The removal of misincorporated bases allows for greater primer extension.

BRIEF DESCRIPTION OF THE DRAWINGS

FIG. 2 shows the use of adapters to convert DNA fragments into a form that can be utilized as rolling circle amplification templates by ligation of hairpin forming adapters to the ends of the fragments. The adapters contain self-complementary sequences at their 3' and 5' ends such that they form stem and loop structures. Furthermore, the stem portion of the hairpin structures create blunt or overhanging ends that allow the adapter to be ligated to the end of any DNA fragments having the appropriate end. By ligating such adapters to both ends of the DNA fragments, the fragments are converted to a circular form which can be utilized as the template for an RCA reaction. Also, the loop portion of the adapters provide a single-stranded region to which the RCA primer can be annealed.

DETAILED DESCRIPTION OF THE INVENTION

This invention provides for the amplification of specific DNA sequences by RCA. In one embodiment, heterohybrid DNA is treated using GMS (Nelson, et al., cited above and U.S. Pat. No. 5,556,750 to Modrich, et al.). The procedure allows for the MutSLH nicking of DNA fragments containing mismatched bases as a means to analyze polymorphism between DNA samples. An improved method for utilizing the MutSLH-generated nick in a DNA amplification strategy is provided here in which the 3'-OH at the nick is used as a primer for a DNA polymerase. The DNA polymerase must replicate a double-stranded DNA template in such a reaction. Therefore it must have strand displacing capability in which it can extend the 3'-OH end of the nick while melting the downstream double-stranded template. DNA pol III can be used for this step as can other DNA polymerases, some of which have greater ability than pol III to initiate strand displacement at a nick. Two or more DNA polymerases can also be combined in order to take advantages of each polymerase. In the case where one of the polymerases has a 3'→5' exonuclease activity, the reaction is improved by the removal of misincorporated nucleotides.

In a typical practice of a method of the invention, at least one DNA sample is methylated and a second DNA sample is not methylated. The samples are then cut with a restriction endonuclease such as Pvu 1, mixed together, denatured and then reannealed to form heterohybrid DNA. Any DNA sample may be subjected to the methods of the invention including genomic DNA, genomic fragments, cDNA, cDNA fragments, and mixtures of these.

Figure 1A:
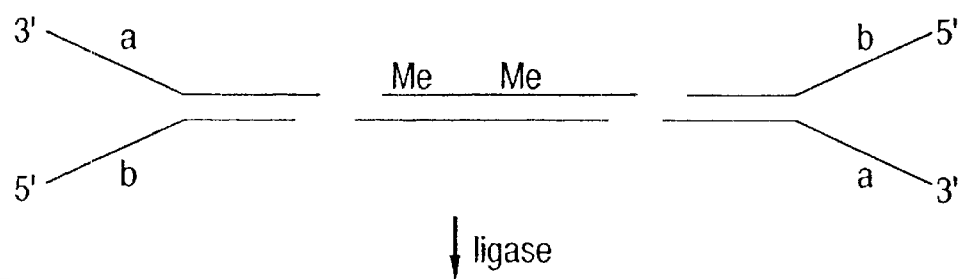
FIG. 1 Adapters are ligated to DNA fragments to obtain fragment-plus-adapter constructs (FIG. 1A); ligation products are shown in FIG. 1B; the adapter-fragment constructs are then subjected to nicking by the MutSLH proteins (FIG. 1C); the nicked fragments are subsequently subjected to a DNA polymerase reaction in which the 3'-OH at the nick is elongated (FIG. 1C and FIG. 1D); as a result of the adapters, the 3'-end of the extended strand (FIG. 1D, c') will be complementary to the Y-region of the other strand; a "splint oligonucleotide" can be used to circularize the DNA (FIG. 1E); if the DNA is circularized so that its two ends are brought together at a nick, then the ends can be ligated together by DNA ligase forming a covalently closed circle (FIG. 1F). A partially double-stranded adapter is used to circularize a double stranded DNA fragment for use as an RCA template. The adapter which has appropriate overhangs on its ends to allow ligation to both ends of the DNA fragment (FIG. 1G) can be used such that annealing of the ends results in a circularized adapter-fragment construct (FIG. 1H) and ligation seals the nicks (FIG. 1I); a single-stranded gap (FIG. 1G), or a nick, located in an internal region of the adapter, provides a 3'-OH (FIG. 1G) that can serve as a primer for DNA polymerase (FIG. 1J); the presence of a non-complementary 5'-tail (FIG. 1J) facilitates the initiation of strand displacement synthesis in which a DNA polymerase invades the duplex region of the DNA template (FIG. 1K). An alternative method for copying a sequence of DNA in an RCA is to use a padlock DNA annealed to the target fragment (FIG. 1L) to create a single stranded gap; extension of the 3'-OH of the padlock DNA followed by ligation results in the circularization of the padlock which is linked to the target DNA (FIG. 1M); an RCA primer is annealed to the padlock DNA (FIG. 1N) for the priming of DNA synthesis; the RCA primer can have a non-complementary 5'-tail that facilitates the initiation of strand displacement at a nick (FIG. 1N).
Figure 1B:
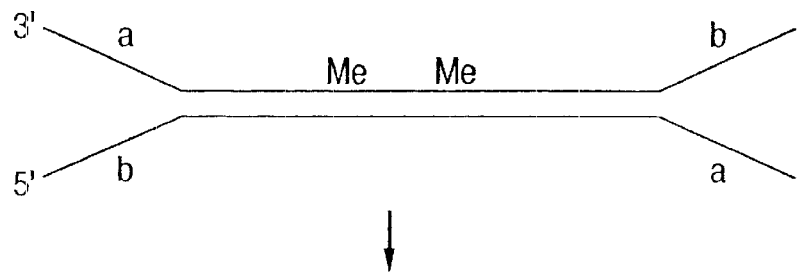

Adapters are then ligated to the fragments to obtain fragment-plus-adapter constructs (FIG. 1A). Linear or Y-shaped adapters may be employed. Y-shaped adapters (FIG. 1A) are used in many preferred embodiments, but, in some cases, where Y-shaped adapters are illustrated, the methods can also be adapted to conventional linear adapters. Y-shaped adapters have been described (see Prashar, Y., and Weissman, S., *Proc. Natl. Acad Sci. USA*, 1996, 93:659–663). A Y-shaped adapter typically has an overhang at one end for ligation to a DNA fragment, and, at the other end, a stretch of noncomplementary sequence on the opposite strands, giving rise to its Y-shape. It is an advantage of the invention that, in preferred embodiments, the Y-shaped adapters allow for the synthesis of non-overlapping subsets of DNA. In typical embodiments, if the invention is carried out with conventional, linear primers, then the PCR-generated subsets will be partially overlapping, that is, some DNA sequences will be represented in more than one subset. It is another advantage of the invention that Y-shaped adapters allow for the synthesis of a DNA fragment of unique sequence by using a GMS generated nick as a primer as described below.

Figure 1C:
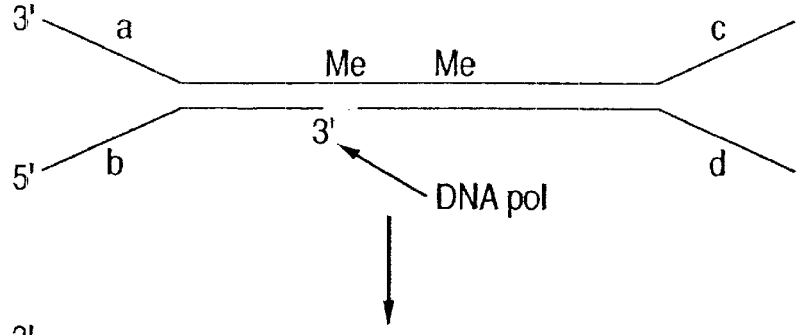
Figure 1D:
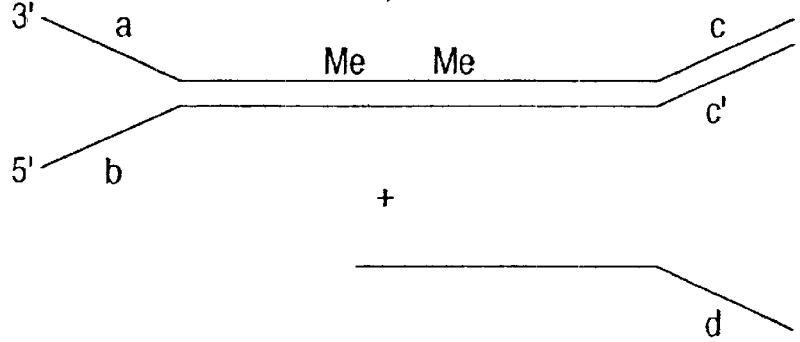

The adapter-fragment constructs are then subjected to nicking by the MutSLH proteins (FIG. 1C). The nicked fragments are subsequently subjected to a DNA polymerase reaction in which the 3'-OH at the nick is elongated (FIGS. 1C and D). As a result of the adapters, the 3'-end of the extended strand (FIG. 1D, c') will be complementary to the Y-region of the other strand. Therefore, all DNAs nicked by MutSLH and subjected to elongation of the 3'-OH can be selected for by the unique combination of sequences at the ends.

In some embodiments, a "splint oligonucleotide" is designed for purposes of circularizing the DNA (FIG. 1E). A "splint oligonucleotide" is a single-stranded sequence complementary to the ends of the DNA that results from extension of the nick (FIG. 1D) such that denaturation of the DNA and annealing of the splint to the extended strand circularizes it. If the DNA is circularized so that its two ends are brought together at a nick, then the ends can be ligated together by DNA ligase forming a covalently closed circle (FIG. 1F). This DNA can then be amplified in an RCA either by extension of the 3'-OH of the splint or by annealing of another primer to the circularized DNA (FIG. 1F). Either the splint or another primer can have a region of DNA sequence at its 5'-end that is not complementary to the template (FIG. 1E) and, therefore, can facilitate initiation of RCA (FIG. 1F). This is because, following extension of the primer once around the DNA template, the non-complementary 5'-end of the primer sequence allows easier invasion of the duplex template by the polymerase. (See reviews by Hingorani, M. M., and O'Donnell, M., *Current Biology*, 1998, 8:R83–86 and by Kelman, Z., et al., cited above).

Another aspect of this invention is that embodiments using DNA polymerase III holoenzyme derived from *E. coli* or other bacteria, including gram-positive and gram-negative bacteria, or related DNA polymerases from eukaryotes that have clamp and clamp loader components (Kornberg and Baker and Kelman and O'Donnell, cited above) can be employed as the DNA polyinerase in RCA. Use of DNA pol III in preferred embodiments provides a greater rate and processivity than other DNA polymerases and provides superior yield and ability to replicate long templates and templates having obstructions to DNA replication such as high GC content, or unfavorable secondary structure or sequence context. Two or more DNA polymerases, including DNA pol III, can also be combined in order to take advantages of each of polymerase's properties. The *E. coli* dnaB and dnaC proteins or other helicases and the single-stranded DNA binding protein (SSB) can also be used to improve rate and strand displacement (Kornberg and Baker, cited above).

As summarized above, this invention also advantageously provides methods for producing approximately equimolar rolling circle amplification of DNA fragment mixtures. The methods are applicable to RCA of any DNA including for purposes of detection, cloning, generation of probes, GMS procedures, DNA mapping, sequencing, and genotyping. In one procedure a pause site is created by the introduction of one or more abasic sites in the template. DNA polymerases are slowed but not completely blocked by such a site. They will tend to insert a nucleotide opposite the abasic site (Randell, cited above). The pause site can be introduced into the template by standard procedures for ligating a fragment containing the pause site into a double-stranded DNA.

Another approach is to circularize a single-strand DNA target fragment with a splint that contains the pause site in a double-stranded internal segment and that has single-stranded ends complementary to the ends of the target fragment. Ligation of this construct results in the insertion of the abasic sequence into the target fragment. Another method is to insert a sequence containing one or more uracils as bases and then creating abasic sites by treatment with uracil glycosylase (UDG, Kornberg and Baker, cited above). The method is also applicable for other types of pause sites such as hairpin structures or protein binding sites on the DNA.

Figure 1G:
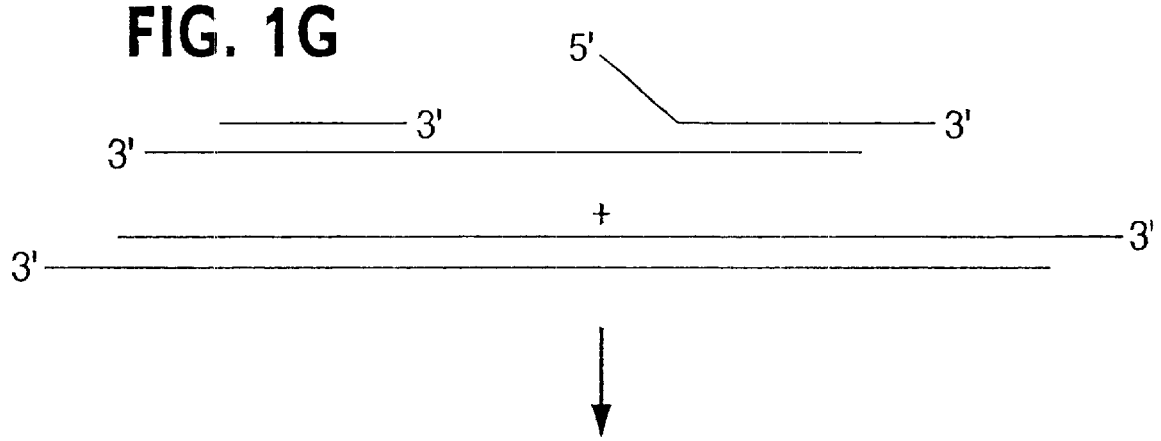
Figure 1H:
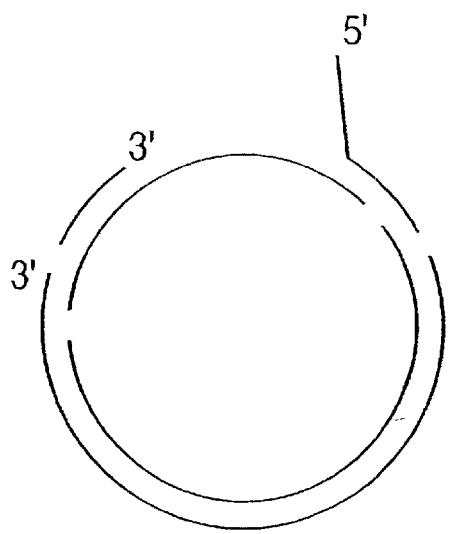
Figure 1I:
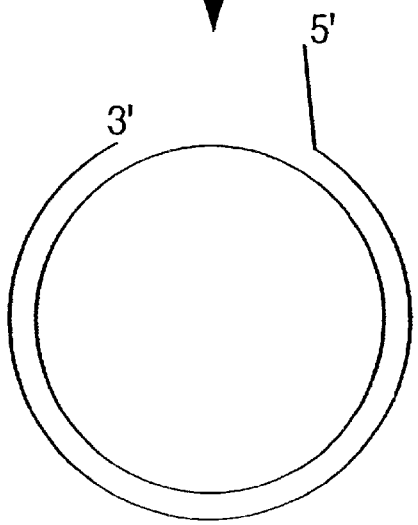

As a general method for amplifying any DNA fragment, an adapter is described that allows for circularization of the fragment and subsequent RCA. The adapter has appropriate overhangs on its ends to allow ligation to both ends of the DNA fragment (FIG. 1G) such that annealing of the ends results in a circularized adapter-fragment construct (FIG. 1H) and ligation seals the nicks (FIG. 1I). The adapter also provides for the ability to prime RCA. A single-stranded gap (FIG. 1G), or a nick, located in an internal region of the adapter, provides a 3'-OH (FIG. 1G) that can serve as a primer for DNA polymerase (FIG. 1J). The presence of a non-complementary 5'-tail (FIG. 1J) facilitates the initiation of strand displacement synthesis in which a DNA polymerase invades the duplex region of the DNA template (FIG. 1K). Embodiments of this invention employ DNA pol III to improve the rate and processivity of the RCA.

Figure 1L:
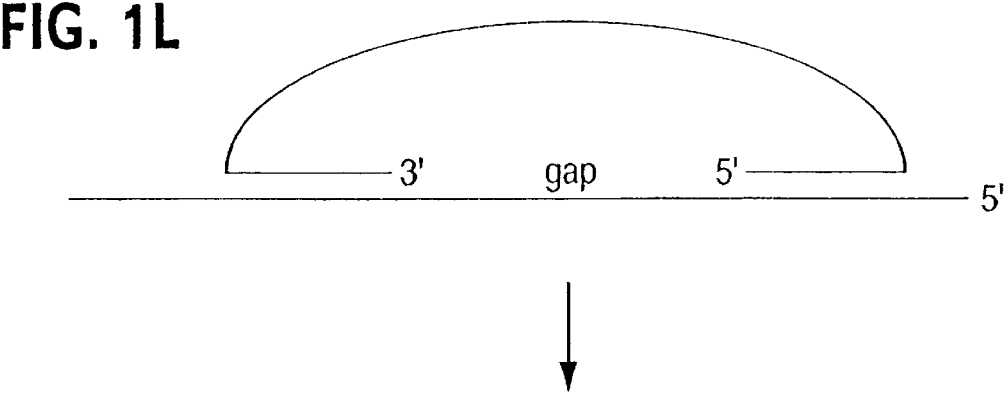
Figure 1M:
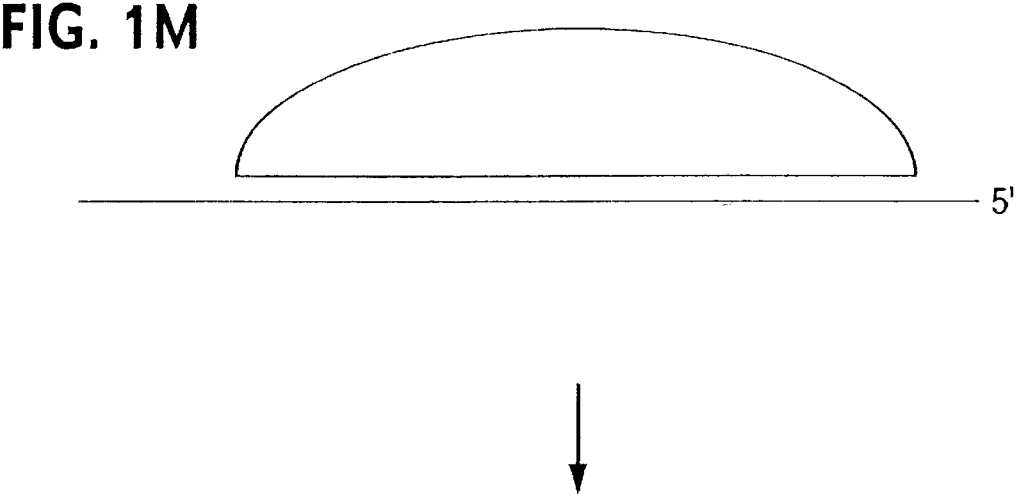

A method is also given for the use of DNA polymerase III for RCA using the padlock method (Nilsson, M., et al., cited above). When the padlock DNA is annealed to the target fragment (FIG. 1L) a single stranded gap is created. Extension of the 3'-OH of the padlock DNA followed by ligation results in the circularization of the padlock which is linked to the target DNA (FIG. 1M). In some cases, it is desirable to have a large gap length in order to amplify a large region of the target DNA. An advantage of this invention is that use DNA polymerase III in the extension step allows for a larger single-stranded gap length because of its superior rate and processivity. Particularly for gaps of several hundred to greater then a megabase, pol III provides greater rates and yields. Another advantage of pol III is that it has very slow rates of initiating strand displacement at a nick compared to other DNA polymerases (O'Donnell, M., and Kornberg, A., *J. Biol. Chem.*, 1985, 260:12884). Therefore, pol III will tend not to displace the 5'-end of the padlock DNA prior to ligation.

Figure 1N:
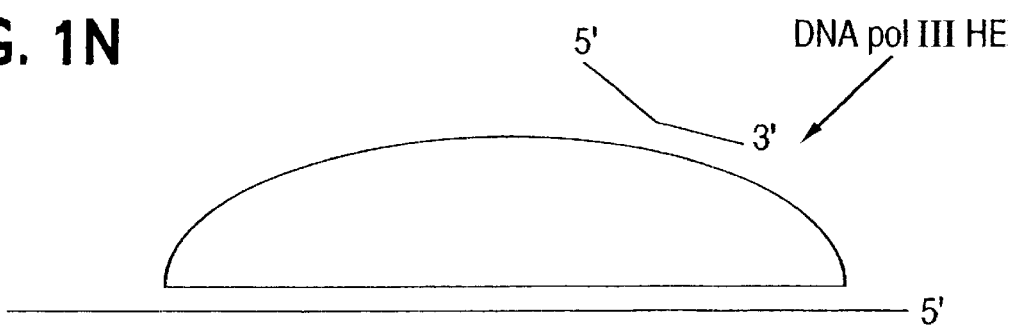

Following circularization, an RCA primer is annealed to the padlock DNA (FIG. 1N) for the priming of DNA synthesis. Pol III is also employed for this reaction because of advantages in RCA mentioned above. The RCA primer can have a non-complementary 5'-tail that facilitates the initiation of strand displacement at a nick (FIG. 1N). Once RCA is initiated, DNA pol III provides superior rates and processivity for strand displacement synthesis.

A general method is also given for polymorphism analysis of repeat sequences such as di- and tri-nucleotide repeats and other microsatellite sequences which are frequently used because of their high level of polymorphism. By amplifying the sequences in an RCA, artifacts associated with PCR are reduced. In PCR reactions, slippage of the DNA polymerase results in accumulating errors, usually by addition or deletion of the repeated sequence. Because RCA is a linear amplification in which the same DNA template is repeatedly copied, replication errors do not accumulate exponentially as they do in a PCR in which the product DNA of one cycle can serve as the template in a subsequent cycle. The use of DNA polymerase III in the reaction reduces the errors because of the highly processive synthesis and fidelity of the enzyme (Kornberg and Baker, cited above).

In another embodiment of the invention, methods are given for converting DNA fragments into a form that can be utilized as RCA templates by ligation of hairpin forming adapters to the ends of the fragments (FIG. 2). The adapters contain self-complementary sequences at their 3' and 5' ends such that they form stem and loop structures. Furthermore, the stem portion of the hairpin structures create blunt or overhanging ends that allow the adapter to be ligated to the end of any DNA fragments having the appropriate end. By ligating such adapters to both ends of the DNA fragments, the fragments are converted to a circular form which can be utilized as the template for an RCA reaction. Also, the loop portion of the adapters provide a single-stranded region to which the RCA primer can be annealed.

The constructs formed can be amplified in an RCA using a primer complementary to the adapters. The method allows for a whole genome amplification in which a subset of DNA segments derived from the original DNA sample are amplified.

Another invention uses two or more DNA polymerases in an RCA reaction. At least one of the DNA polymerases possesses a 3'–5' exonuclease proofreading activity capable of correcting base mispairs. The removal of misincorporated bases allows for greater primer extension.

EXAMPLES

Example 1

Figure 3:
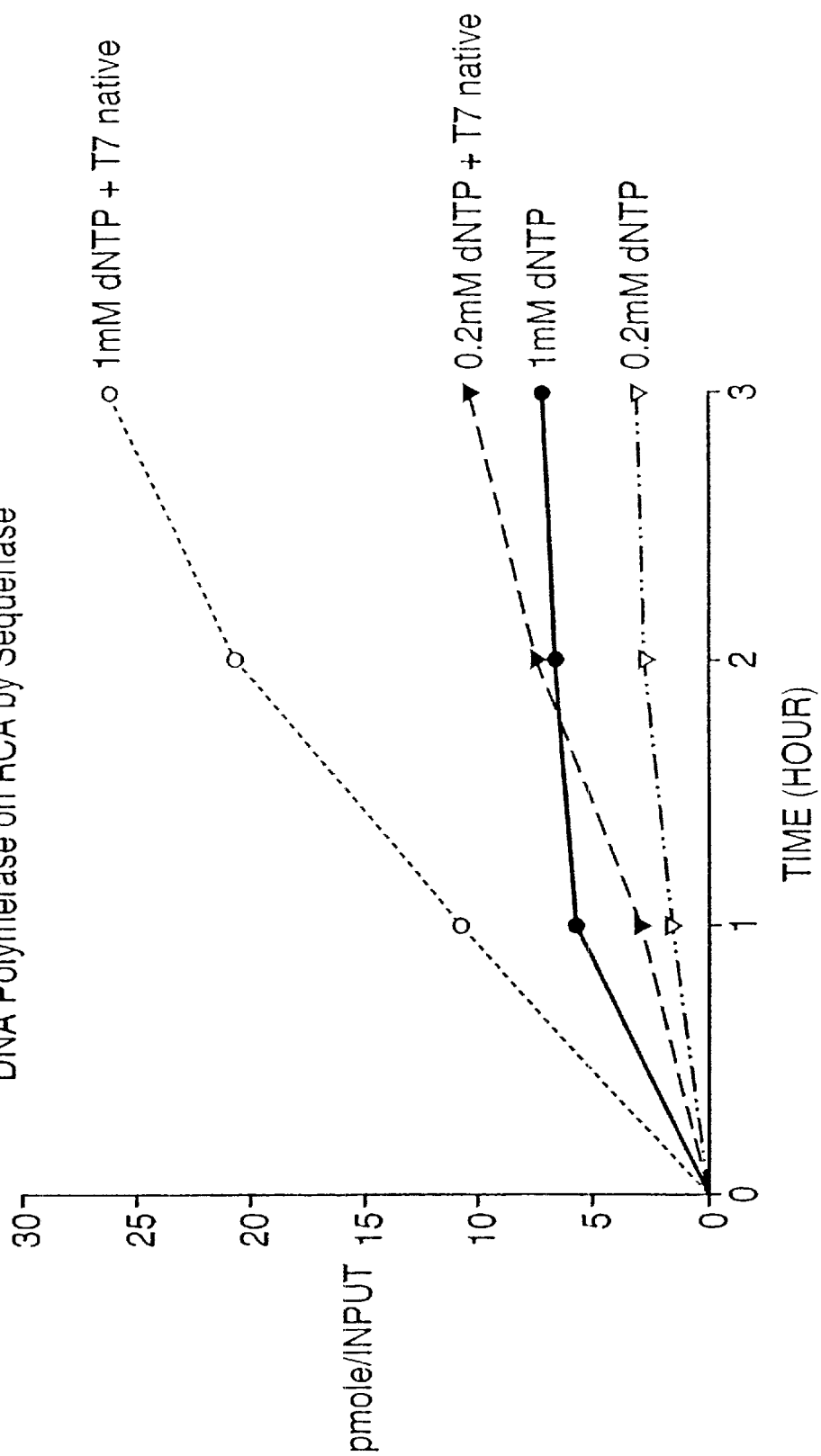
FIG. 3 shows the effect of dNTP concentration and T7 native DNA polymerase on rolling circle amplification by SEQUENASE™.

Effect of T7 Native DNA Polymerase (with 3'–5' exonuclease) and of Deoxynucleotide Concentration on M13 Rolling Circle Amplification This example demonstrates that the presence of a small amount of the native T7 DNA polymerase, which contains a 3'–5' exonuclease, stimulates the maximum rate of synthesis by sequenase (FIG. 3). Sequenase is present at a saturating concentration (26 units) and so it is concluded that the T7 polymerase is not stimulating the reaction by simply increasing the total DNA polymerase units in the reaction. Rather, it is concluded that T7 polymerase is stimulating the reaction by removing mismatched nucleotides which block primer extension. RCA reactions were performed at 37° C. and aliquots were removed at 1, 2, and 3 hours, as indicated, in a reaction volume of 50 microliters containing 20 mM Tris-acetate, 10 mM magnesium acetate, and 50 mM potassium acetate, pH 7.9 @ 25° C., 0.2 mM or 1.0 mM each deoxynucleoside triphosphate, as indicated, 2 uCi 5'-[$-^{32}$P] dCTP (Amersham Pharmacia Biotech), 30 ng of M13 singly-primed single-stranded M13 DNA (see below), 4.2 micrograms of *E. coli* single-strand DNA binding protein (Studwell & O'Donnell, J. Biol. Chem. 265:1175–1178, 1990), 26 units of Sequenase 2.0 (United States Biochemical), and 0.5 unit of T7 native DNA polymerase, cloned (United States Biochemical), as indicated. Aliquots (4 ul) were spotted onto DE81 filter paper and deoxynucleotide incorporation was determined.

Singly-primed single-stranded M13 viral (+) strand DNA. Annealing reactions (100 microliters) contained 20 mM Tris-HCl pH 7.5, 40 mM NaCl, 500 nM primer F4 and 6.5 microliters M13 viral (+) strand DNA (27.6 nM M13 single-strand DNA circles). Reactions were heated to 95° C. for 1 min and cooled slowly over 30 min. The primer:circle ratio=18. Primer F4 (5'-TCT GTT TAT AGG GCC TCT TCG CTA TTA CGC CAG C-3') consisted of 24 nucleotides at the 3' end complementary to M13mp19 (+) strand, and 10 nucleotides non-complementary at the 5' end. The 3' end is at M13 map position 6377.

Example 2

Figure 4:
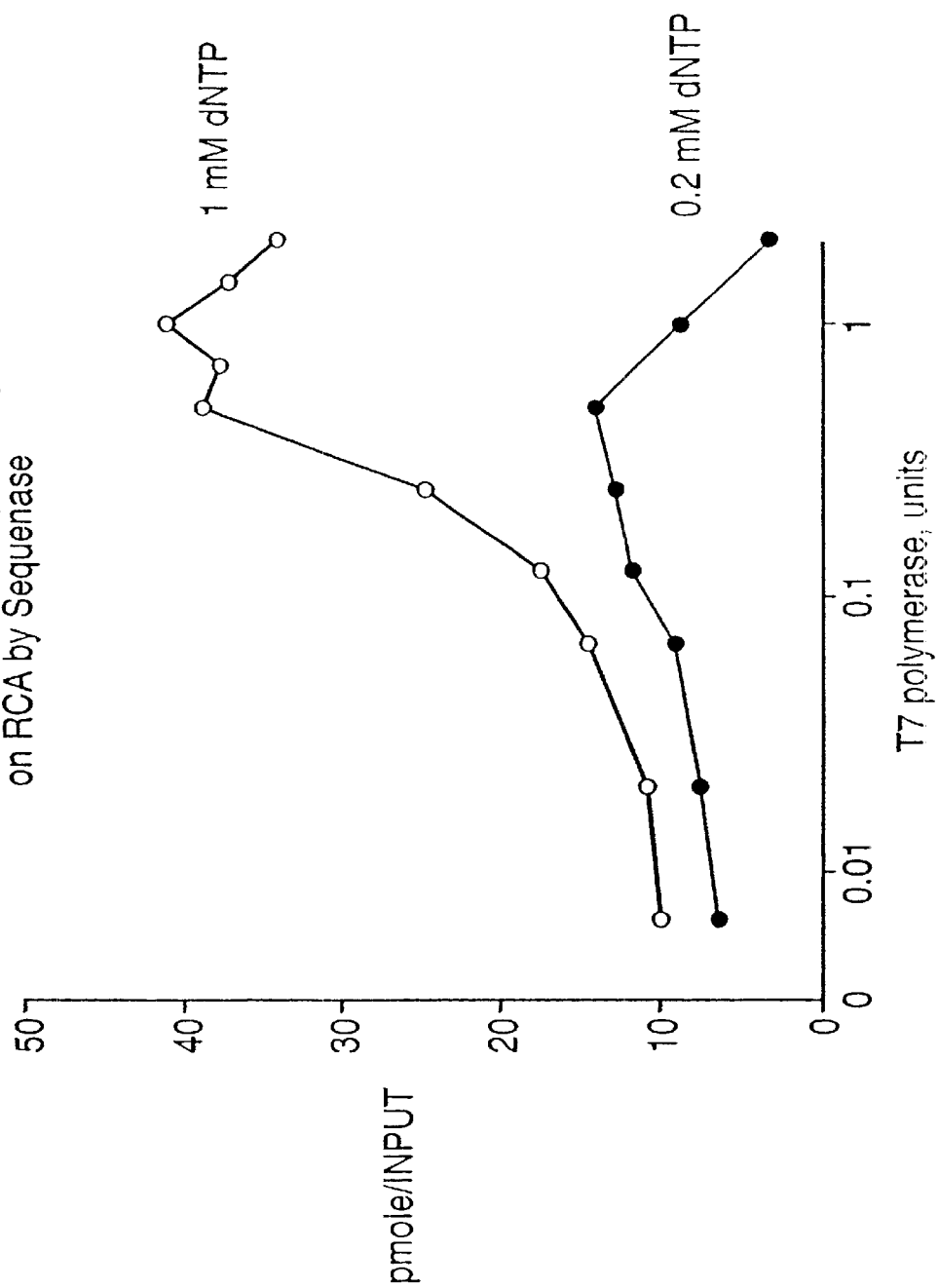
FIG. 4 shows the effect of mismatch correction by T7 native DNA polymerase on rolling circle amplification by SEQUENASE™.

Effect of T7 Native DNA Polymerase (with 3'–5' exonuclease) Concentration on M13 Rolling Circle Amplification This example shows the dependence on T7 DNA polymerase concentration of the stimulation of RCA reactions using sequenase (FIG. 4). RCA reactions were performed for 3 hr as described in Example 1 except that T7 native polymerase was added as indicated. Aliquots (4 ul) were spotted onto DE81 filter paper and deoxynucleotide incorporation was determined.

Example 3

Rolling Circle Amplification (RCA) Assay using reconstituted DNA polymerase III holoenzyme (Kelman and O'Donnell, *Annu. Rev. Biochem.* 64: 171–200, 1995), and accessory replication proteins including DnaB helicase (Arai et al., *J. Biol. Chem.* 256: 5247–5252, 1981), DnaG primase (Rowen and Kornberg, *J. Biol. Chem.* 253:

758–764, 1978) and SSB (Studwell and O'Donnell, *J. Biol. Chem.* 265:1175–1178, 1990).

Figure 5:
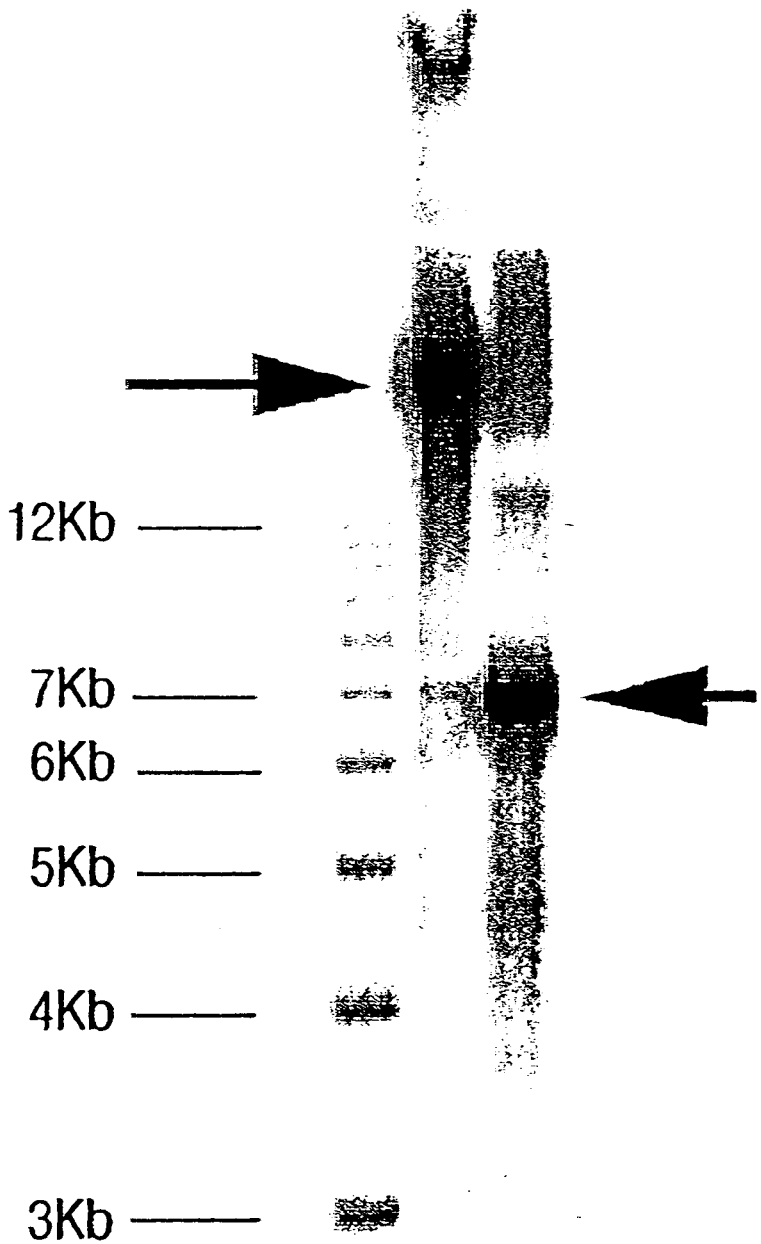
FIG. 5 shows product formed using DNA polymerase III holoenzyme and primed M13 single-stranded DNA as the template. The product strands are larger than 12 kb (see the arrow for (−) EcoR I). To prove that the product DNA consisted of tandem repeats of the M13 sequence, as predicted for an RCA reaction, the reaction products were digested with EcoR 1 which converted the product DNA to unit lengths of 7250 kb (FIG. 3, (+) EcoR 1).

This example demonstrates the product formed using DNA polymerase III holoenzyme and primed M13 single-stranded DNA as the template. The product strands are larger than 12 kb (see the arrow in FIG. 5, for (−) EcoR I). To prove that the product DNA consisted of tandem repeats of the M13 sequence, as predicted for an RCA reaction, the reaction products were digested with EcoR 1 which converted the product DNA to unit lengths of 7250 kb (FIG. 3, (+) EcoR 1).

RCA assays were in 50 μl of Reaction buffer (HEPES-NaOH (pH7.4), 12 mM $MgCl_2$, 5 mM DTT, 100 μg BSA/ml, 5 mM ATP, 20% Glycerol (v/v)) containing 325 ng (138 fmol) M13mp19 (+) ssDNA as template, 2.5 pmol of F4 primer (5'-TCT GTT TAT AGG GCC TCT TCG CTA TTA CGC CAG C-3', the underlined sequence annealed to position 6377–6400 on M13mp19 (+) strand), 1.25 pmol (as dimer) of β clamp, 1 pmol of Pol III*, 5.5 pmol (as hexamer) of DnaB (helicase), 15.4 pmol of DnaG primase), 54.2 pmol (as tetramer) of SSB, 50 nM each ATP, UTP, GTP, and CTP, 400 μM each dATP, dTTP, dGTP, and $\alpha^{32}P$-CTP (3000–6000 cpm/pmol). All additions were made at 0° C., and then reactions were shifted to 37° C. and quenched with EDTA at a final concentration of 67 mM after 1 hour incubation at 37° C. An aliquot of amplification products was quantitated by spotting onto DE81 filters as described (Rowen and Kornberg, 1978). After washing and drying, the filters were counted in a liquid scintillation counter (Packard). Another aliquot (2 μl) was digested with EcoR I or incubated with only EcoR I buffer at 37° C. for 1 hour. The digestion mix was treated with Protease K for 30 minute and then analyzed on a 0.7% alkaline gel followed by exposing to storage Phosphor screen and quantitated using ImageQuant software (Molecular Dynamics).

The above description is for the purpose of teaching the person of ordinary skill in the art how to practice the present invention, and it is not intended to detail all those obvious modifications and variations of it which will become apparent to the skilled worker upon reading the description. There are numerous variations of steps in the overall procedures, and for preparing the probes. In some embodiments, for example, the primer or DNA fragment is tagged with biotin or the like and captured with strepavidin or avidin or the like using standard procedures (Geschwind, D. H., et al., *Genetic Analysis,* 1996, 13:105–111). Selective cleavage of DNA using RecA-assisted restriction endonuclease (RARE) may be employed (Ferrin, L. J., and Camerini-Otero, R. D., *Science,* 1991, 254:1494–1497). It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers, books and patents cited herein are expressly incorporated in their entireties by reference.

What is claimed is:

1. A method of circularizing and amplifying large fragments of DNA comprising:
   (a) providing a DNA-adapter construct which has a DNA fragment ligated to an adapter, wherein the adapter comprises first, second, and third oligonucleotides, wherein the first and the second oligonucleotides are annealed to the third oligonucleotide, wherein a gap is present between the first and the second oligonucleotides annealed to the third oligonucleotide, and wherein the second oligonucleotide has a 5' region present at the gap that is noncomplementary to the third oligonucleotide, and wherein first and second ends of the DNA fragment are ligated to first and second ends of the adapter to form a circle; and
   (b) amplifying the DNA-adapter construct using DNA pol III in a rolling circle amplification.

2. A method according to claim 1 in which rolling circle amplification is performed in the presence of a polypeptide selected from the group consisting of dnaB, dnaG, dnaC, other helicases, SSB, and mixtures thereof.

3. A method according to claim 1 wherein a primer is used in step (b) which has, at its 3'-end, a base complementary to an allelic variant of a heterozygous marker site wherein the allelic variant is present in the DNA fragment.

4. A method according to any one of claims 1 to 3 in which a single-strand DNA product of the rolling circle amplification is used as a template for subsequent DNA synthesis by primer extension or hyperbranching synthesis.

5. A method according to claim 4 wherein the subsequent DNA synthesis is performed using primers with 3'-ends complementary to an allelic variant of a heterozygous marker, wherein the allelic variant is present in the fragment.

6. A method of circularizing and amplifying large fragments of DNA comprising:

providing a DNA-adapter construct which has a double-stranded DNA fragment ligated to an adapter, wherein the adapter (a) lacks a phosphate at one end, (b) has a 3'-dideoxy terminus or other terminal group that blocks extension by a DNA polymerase, or (c) has an internal gap, wherein a first strand but not a second strand of the DNA fragment is circularized by the adapter;

amplifying the DNA-adapter construct using DNA pol III in a rolling circle amplification reaction to form a single-stranded amplification product; and amplifying the single-stranded amplification product with a primer complementary at its 3' end to an allelic form of a heterozygous marker, wherein the allelic form is present in the DNA fragment.

* * * * *

SEQUENCE LISTING

<160> NUMBER OF SEQ ID NOS: 1

<210> SEQ ID NO 1
<211> LENGTH: 34
<212> TYPE: DNA
<213> ORGANISM: Artificial Sequence
<220> FEATURE:
<223> OTHER INFORMATION: 24 nucleotides at the 3' end complementary to
    M13mp19(+) (at map position 6377) and 10
    nucleotides non-complementary at the 5' end

<400> SEQUENCE: 1
tctgtttata gggcctcttc gctattacgc cagc                          34